US 8,771,656 B2
Jul. 8, 2014

(12) United States Patent
Howell et al.

(54) LONG-LASTING EASY WASH-OFF COSMETIC COMPOSITIONS

(75) Inventors: Ashley L. Howell, Oakland, NJ (US); Bing C. Mei, Mahwah, NJ (US)

(73) Assignee: Avon Products, Inc, New York, NY (US)

( * ) Notice: Subject to any disclaimer, the term of this patent is extended or adjusted under 35 U.S.C. 154(b) by 0 days.

(21) Appl. No.: 13/325,670

(22) Filed: Dec. 14, 2011

(65) Prior Publication Data

US 2013/0156714 A1 Jun. 20, 2013

(51) Int. Cl.
*A61Q 1/02* (2006.01)
(52) U.S. Cl.
CPC ........................................ *A61Q 1/02* (2013.01)
USPC .................. 424/64; 424/63; 424/70
(58) Field of Classification Search
CPC .................................... A61Q 1/02; A61Q 1/10
USPC .................................................. 424/64, 63, 70
See application file for complete search history.

(56) References Cited

U.S. PATENT DOCUMENTS

| | | | |
|---|---|---|---|
| 4,795,631 A * | 1/1989 | Sheehan | 424/64 |
| 4,976,961 A | 12/1990 | Norbury et al. | |
| 5,993,831 A | 11/1999 | Ribier et al. | |
| 6,228,354 B1 * | 5/2001 | Jeng | 424/78.07 |
| 6,296,858 B1 | 10/2001 | Agostini et al. | |
| 6,592,854 B1 | 7/2003 | Dupuis | |
| 7,053,034 B2 | 5/2006 | Shefer et al. | |
| 7,323,162 B2 | 1/2008 | Martin et al. | |
| 7,632,905 B2 | 12/2009 | Boupat et al. | |
| 2005/0186169 A1 | 8/2005 | Charbit | |
| 2006/0127427 A1 | 6/2006 | Vernice et al. | |
| 2007/0231355 A1 * | 10/2007 | Quadir et al. | 424/401 |
| 2008/0262122 A1 | 10/2008 | Ueno et al. | |
| 2011/0268688 A1 | 11/2011 | McCarthy et al. | |
| 2012/0213725 A1 | 8/2012 | Galleguillos et al. | |
| 2012/0301416 A1 | 11/2012 | Marotta et al. | |

FOREIGN PATENT DOCUMENTS

| | | |
|---|---|---|
| EP | 0011806 B1 | 6/1980 |
| EP | 0705854 A1 | 4/1996 |
| WO | 2008074675 A1 | 6/2008 |
| WO | 2008122993 A1 | 10/2008 |
| WO | 2009118763 A1 | 10/2009 |
| WO | 2012/156965 A1 | 11/2012 |

OTHER PUBLICATIONS

Lubrizol Standard Test Procedure, Aug. 2006 edition, published by Lubrizol Corpooration.*
Specification Eudragit L 100 and Eudragit S 500; Rohm GmbH & Co. K.G., Sep. 2004.

* cited by examiner

*Primary Examiner* — Richard Schnizer
*Assistant Examiner* — Yanzhi Zhang
(74) *Attorney, Agent, or Firm* — David M. Joyal; Joan M. McGillycuddy

(57) ABSTRACT

Cosmetic compositions are provided, which are capable of forming a cosmetic film on a human integument when applied thereto. Cosmetic compositions according to the invention typically include a cosmetically acceptable vehicle, optionally, one or more colorants, and a pH-dependent film-forming polymer of poly(methacrylic acid-co-methyl methacrylate) having a ratio of methacrylic acid to methyl methacrylate of about 1:1 to about 1:2, an acid value of from about 150 to about 350 mg KOH/g, and a weight average molar mass between about 100,000 and about 150,000 g/mol. The compositions are capable of forming an adherent film on the integument that is substantially resistant to removal by water at a first pH, but readily dispersible or soluble in water at a second pH higher than said first pH.

18 Claims, No Drawings

LONG-LASTING EASY WASH-OFF COSMETIC COMPOSITIONS

FIELD OF THE INVENTION

The present application generally relates to cosmetic compositions that form long-lasting deposits on a human integument, yet are easily removable by modulating the pH. More particularly, the application relates to cosmetic compositions having pH-dependent polymers that are capable of forming an adherent film on a human integument that is substantially resistant to removal by water at a first pH but is readily removable at a second pH.

BACKGROUND

With conventional cosmetic products, a user typically must choose between a product that is easily removable and a product that remains on the skin for long periods of time (i.e., an entire day). Although easily-removable products can be rapidly removed by, for example, washing with soap and water, a user may find herself repeatedly reapplying the product throughout the day, as the product may also be inadvertently removed by sweat and contact with clothing or the like. On the other hand, typical long-lasting cosmetic products are less subject to inadvertent removal, but may be difficult to wash off and may require the use of organic solvents or other harsh cosmetic removers. Accordingly, there is a continuing need in the art for cosmetic compositions that remain on the skin for extended periods of time, while being easily-removable by washing with soap and water.

Certain pH-dependent products are known in the art. For example, U.S. Pat. No. 5,993,831 to Ribier et al., incorporated herein by reference in its entirety, is directed to compositions containing nanoparticles of one or more pH-dependent polymers encapsulating an oily phase containing an active agent such as a cosmetic or pharmaceutical. The nanoparticles are said to be from 100 to 1000 nm in diameter, which allows the particles to slip between the outermost corneocytes of the stratum corneum without reaching the living epidermis.

As another example, U.S. Pat. No. 4,976,961 to Norbury et al., incorporated herein by reference in its entirety, is similarly directed to cosmetic emollient oils in microcapsules of pH-dependent polymers. Norbury's microcapsules are said to range in size from 50 to 2000 μm in diameter, and are typically crushed on the skin to release the oils contained therein. The microcapsule shell is said to include organic polymers such as phenolic aldehydes, urea-aldehyes, acrylic polymers, gelatin, and agar.

U.S. Pat. No. 7,053,034 to Shefer et al., incorporated herein by reference in its entirety, is directed to a controlled-release carrier system for targeted delivery of fragrances and active ingredients onto fabric, hair, and skin. Shefer's system is said to include solid hydrophobic nano-spheres encapsulated in a pH or salt sensitive micro-spheres. The micro-spheres are described as having an average sphere size in the range of from about 20 μm (micrometers) to about 100 μm, and the nano-spheres are said to have an average sphere size in the range of from about 0.01 μm to about 5 μm. Moreover, the micro-spheres may be made from such exemplary pH-sensitive materials as copolymers of acrylate polymers with amino substituents, acrylic acid esters, and polyacrylamides. The micro-spheres of Shefer are formed from high temperature melts emulsified into an aqueous phase.

U.S. Patent App. Pub. 2006/0127427 to Vernice et at, incorporated herein by reference in its entirety, describes a surface coated abrasive material, having a water-soluble abrasive core surrounded by a coating that is substantially insoluble in aqueous media during storage but becomes substantially water soluble upon application of substantially large quantities of water or adjustment of the pH of the aqueous medium.

The cited art fails to recognize that pH-dependent polymers can advantageously provide long-wear cosmetic films that are readily removed under mild conditions by altering the pH. Accordingly, there is a continuing need in the art for pH-dependent cosmetic compositions that remain on the skin for extended periods of time, while being easily-removable, for example, by washing with soap and water.

SUMMARY OF THE INVENTION

It has surprisingly been found that certain film-forming, pH-dependent polymers may be employed within cosmetic compositions to increase wear time of the compositions, while still allowing for removal of the same under mild, aqueous conditions, preferably with soap and water. The cosmetic compositions form substantive, durable films on human integuments, but may be removed by modulating the pH to dissolve or disperse the polymers, such as by washing the skin with water and a surfactant.

In accordance with the foregoing objectives and others, the present invention provides a method for forming a cosmetic film on a human integument. The method includes applying to the human integument a cosmetic composition having a cosmetically acceptable vehicle, optionally, one or more colorants, and a pH-dependent film-forming polymer of poly(methacrylic acid-co-methyl methacrylate).

A specific embodiment of the invention is a method for forming a cosmetic film on a human integument comprising: applying to said human integument a cosmetic composition having a cosmetically acceptable vehicle, optionally, one or more colorants, and a pH-dependent film-forming polymer of poly(methacrylic acid-co-methyl methacrylate) with a ratio of methacrylic acid to methyl methacrylate of about 1:1 to about 1:2, an acid value of from about 150 to about 350 mg KOH/g, and a weight average molar mass between about 100,000 and about 150,000 g/mol, wherein said cosmetic composition is capable of forming an adherent film on said integument that is substantially resistant to removal by water at a first pH, but readily dispersible or soluble in water at a second pH higher than said first pH, with the proviso that said film forming polymer is not in the form of a microcapsule.

In certain embodiments of the invention, the pH-dependent film-forming polymer typically has a molar ratio of methacrylic acid to methyl methacrylate of about 1:1 to about 1:2, an acid value of from about 150 to about 350 mg KOH/g, and a weight average molar mass between about 100,000 and about 150,000 g/mol. Typically the pH-dependent film forming polymer is a copolymer with monomers comprised of acrylic acid/acrylic acid derivatives, such as polymers with the following structure

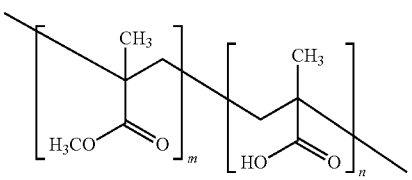

wherein m and n are integers so that the weight average molar mass is between about 100,000 and about 150,000 g/mol and so that the molar ratio of methacrylic acid to methyl methacrylate is about 1:1 to about 1:2. Examples of these polymers are available as ELTDRAGIT® S 100 and EUDRAGIT® L 100 from Evonik Degussa-Huls Corporation.

While the preferred pH-dependent film forming polymers are soluble under basic conditions, it is recognized that solubility under acid conditions, or under different pH modulation conditions, may potentially be of interest in the methods of the invention. An example of such a polymer for acid conditions has the structure

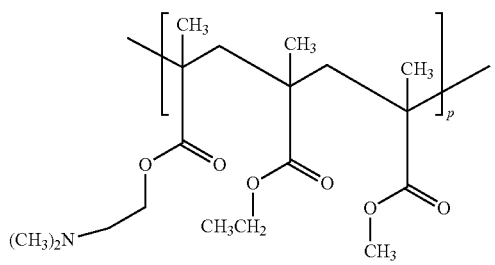

wherein p is an integer so that the weight average molar mass is between about 100,000 and about 150,000 g/mol. Polymers of this type are available from Evonik Degussa-Huls Corporation. Amine functionalized polymers of the type shown above are contemplated to be useful for formulating products characterized by poor solubility under basic conditions, but good solubility under acidic conditions. As the pH of a solution is decreased to the trigger pH, the polymers experience ionization of amine groups, resulting in increased aqueous solubility and consequent dissolution of the polymer and removal from the integument. Accordingly, products of this type are capable of forming a durable, long-wearing film on an integument that is resistant to removal or transfer under basic, and preferably neutral, conditions, including resistance to removal with soap and water.

Generally, the cosmetic composition is capable of forming an adherent film on the integument that is substantially resistant to removal by water at a first pH. However, the polymer is readily dispersible or soluble in water at a second pH that is higher (i.e., more basic) than the first pH. The film forming polymer is not in the form of an encapsulant, e.g., a microcapsule or nanocapsule.

In another aspect of the invention, a cosmetic composition is provided. The cosmetic composition includes a cosmetically acceptable vehicle, optionally, one or more colorants, and a pH-dependent film-forming polymer of poly(methacrylic acid-co-methyl methacrylate). The polymer typically has a ratio of methacrylic acid to methyl methacrylate of about 1:1 to about 1:2, an acid value of from about 150 to about 350 mg KOH/g, and a weight average molar mass between about 100,000 and about 150,000 g/mol. Moreover, the polymer is capable of forming an adherent film on a human integument that is substantially resistant to removal by water at a first pH. However, the polymer is dispersible or soluble in water at a second pH, which is higher (i.e., more basic) than the first pH. The film forming polymer is not in the form of an encapsulant.

A specific embodiment of the invention is a cosmetic composition comprising a cosmetically acceptable vehicle, optionally, one or more colorants, and a pH-dependent film-forming polymer of poly(methacrylic acid-co-methyl methacrylate) with a ratio of methacrylic acid to methyl methacrylate of about 1:1 to about 1:2, an acid value of from about 150 to about 350 mg KOH/g, and a weight average molar mass between about 100,000 and about 150,000 g/mol, wherein said polymer is capable of forming an adherent film on a human integument that is substantially resistant to removal by water at a first pH, but readily dispersible or soluble in water at a second pH higher than said first pH, with the proviso that said film forming polymer is not in the form of a microcapsule.

These and other aspects of the invention will be better understood by reading the following detailed description and appended claims.

DETAILED DESCRIPTION

All terms used herein are intended to have their ordinary meaning in the art unless otherwise provided. All concentrations are in terms of percentage by weight of the specified component relative to the entire weight of the cosmetic composition. Unless otherwise defined, the phrase "substantially free" refers to an amount of a component that is sufficiently low such that the component contributes no significant properties to the bulk and, in any event, will be less than 0.5% by weight and preferably less than 0.1% by weight.

The invention provides cosmetic compositions that may be applied to a human integument (e.g., skin, lashes, lips, hair, etc.) and that may remain thereon for extended periods of time, and yet are easily removed by modulating the pH, such as by washing with soap and water. The cosmetic compositions may be in the form of solids (e.g., powders and pressed powders); suspensions; serums; lotions; aqueous, dilute alcoholic or oily gels; dispersions; emulsions (e.g., oil-in-water emulsions and water-in-oil emulsions); liquids, and the like. As used herein, the term liquid is intended to include very thin to very viscous materials, including non-Newtonian liquids having high initial viscosities (e.g., up to about 2,000,000 cps at 25° C.), as well as gels and other materials capable of being dispensed from a container onto a human integument. Preferred cosmetics include, without limitation, mascara, foundation, sunscreen, hair treatments, press powder, eyeshadow, aqueous lip products (e.g., lipstick and lipgloss), skin cream, skin gel, and the like.

The cosmetic compositions comprise one or more pH-dependent, film-forming polymers. Generally, these polymers comprise anionic copolymers based on methacrylic acid and methyl methacrylate in a random, block, or alternating configuration. The polymers are insoluble in water at a pH below a trigger pH due to non-ionized (i.e., protonated) carboxylic acid groups. However, as the pH of a solution is increased to the trigger pH, the polymers experience ionization of the carboxylic acid group, resulting in increased aqueous solubility and consequent dissolution of the polymer and removal from the integument.

Exemplary pH-dependent polymers according to the invention will comprise methacrylic acid and methyl methacrylate copolymers in a molar ratio of from about 1:1 to about 1:2 (e.g., about 1:1, and about 1:2). The polymers typically comprise an acid value of from about 150 to about 350 trig KOH/g, including exemplary ranges such as, but not limited to, about 150 to about 200 mg KOH/g and about 300 KOH/g to about 350 KOH/g. Acid values of about 190 mg KOH/g and about 315 mg KOH/g are particularly preferred. Moreover, in certain embodiments, the pH-dependent polymers will typically have an average molar mass of from about 100,000 to about 150,000 g/mol, and most typically about 125,000 g/mol.

The preferred pH-dependent film-forming polymers are sold under the names EUDRAGIT® S 100 and EUDRAGIT® L 100 by Evonik Degussa-Huls Corporation. Films or coatings of such polymers are insoluble at pH values less than about 7 (EUDRAGIT® S 100) and less than about 6 (EUDRAGIT® L 100). Accordingly, these polymers may be included in cosmetic compositions either alone or in combination, such that the pH-dependent solubility of a film produced thereby may be selected to be from about 6 to about 7, including but not limited to about 6.0, 6.1, 6.2, 6.3, 6.4, 6.5, 6.6, 6.7, 6.8, 6.9 and 7.0. Such selection will typically be based on the desired use of the cosmetic composition, but it may broadly be stated that the pH-dependent, film-forming polymers will be selected such that the film is insoluble in water at a pH less than that of a soap/water combination (typically greater than about 7). Accordingly, the film-forming polymers may be chosen such that the cosmetic composition is soluble at a pH greater than about 5.0, greater than about 5.5, greater than about 6.0, greater than about 6.5, greater than about 7.0, or greater than about 7.5, depending on the intended use. One of skill in the art would understand that other polymers may be used that are soluble via other pH modulations, i.e., under increasingly acidic conditions.

The amount of pH-dependent polymer(s) present in the compositions will typically range from about 0.2 to about 10% by weight of the composition, but may be higher or lower depending on the desired properties. Typically, the cosmetic compositions will comprise the pH-dependent polymers in an amount of from about 0.2 to about 10% by weight, more typically from about 1 to about 8% by weight, and most typically from about 2 to about 5% by weight. It has been found that cosmetic compositions comprising such pH-dependent polymers are both easy to apply to and remove from the skin, and remain in contact with the skin for long periods of time. For example, cosmetic compositions comprising pH-dependent polymers may remain on the skin for greater than about 4, about 5, about 6, about 7, or even greater than about 8 hours.

The film-forming polymer is not in the form of an encapsulant, and is particularly not utilized such as those described in U.S. Pat. Nos. 7,053,034, 4,976,961, 5,993,831 and U.S. Patent App. Pub. No. 2006/0127427, each of which is described above and incorporated herein by reference in their entirety. As used herein, the term "microcapsule" refers to a structure having a polymeric membrane (i.e., shell) surrounding a core material (e.g., an active ingredient). The term "microcapsule" is intended to be generic, and is not limited to a particular size (i.e., nano, micro, etc.).

In addition to the pH-dependent film forming polymers, the inventive cosmetic compositions may comprise any number of additional ingredients, such as, but not limited to: active ingredients (e.g., cosmetic, dermatological, and/or pharmaceutical), alcohols, allergy inhibitors, amino acids, anti-acne agents (e.g., salicylic acid), anti-aging agents, antiseptics, antifungal agents, antiperspirants, analgesics, anti-hair loss agents, anti-wrinkle agents, antibacterial agents, anti-microbial agents, anti-oxidants, anti-inflammatory agents, burn healing agents, colorants (e.g., lakes, pigments, and the like), de-pigmentation agents, deodorants, dyes, emollient (e.g., glycerin, butylene glycol), excipients, fatty substances, fillers, film formers e.g., dimethicone acrylate copolymer, ethylhexyl acrylate copolymer), fragrances, free radical scavengers, glycerin, glycerin monostearate, glycerin distearate, hair growth agents, hair conditioners, hair softeners, hair moisturizers, herbal extracts, humectants (e.g., hyaluronic acid, orotic acid, lipoprotein), insect repelants, medication, moisturizers, non-active carrier oils (e.g., triglycerides, silicone oils, mineral oils), oils, peptides, polypeptides, proteins, perfumes, pigments, preservatives, plasticizers, reflectants, sebum absorbers, skin lightening agents, sunscreens, surfactants, tanning agents, thickening agents hydroxyethylcellulose, xanthan gum, carbomer), Vaseline, vasoconstrictors, vasodilators, vitamins (e.g., Vitamin A, Vitamin E), water, waxes, and/or combinations thereof.

The composition of the present invention may also include other cosmetic ingredients such as, but not limited to, humectants emollients, moisturizers, anti-wrinkle ingredients, concealers, matte finishing agents, pigments, colorants, proteins, anti-oxidants, bronzers, chelating agents, emulsifiers, ultraviolet (UV) absorbing agents, oil absorbing agents, anti-foam agents, anti-tack agents, thickeners, fragrances, preservatives, anti-microbials, fungistats, neutralizing agents, vitamins, plasticizers, cohesion agents, basifying and acidifying agents, fillers, solvents, and mixtures thereof.

The compositions may contain additional ingredients such as alkalinizing agents, emulsifying agents, emollients, plasticizers, preservatives, humectants, moisturizing agents, solvents, and tonicity agents or active ingredients suitable to provide anti-aging benefits. Examples of preferred additional ingredients include glycerin.

Additional ingredients may optionally be added to the inventive compositions as detailed below.

Colorants or pigments: The compositions may comprise one or more cosmetic powders, for example, calcium aluminum borosilicate, PMMA, polyethylene, polystyrene, methyl methacrylate crosspolymer, nylon-12, ethylene/acrylic acid copolymer, boron nitride, Teflon, silica, or the like. Typically the compositions will include colorants or pigments to impart a desired color or effect, examples are inorganic pigments, organic pigments, and/or lakes. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Non-metal oxides such as alumina and silica, ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like, are also contemplated to be suitable inorganic pigments. Organic pigments can include, but are not limited to, at least one of carbon black, carmine, phthalocyanine blue and green pigment, diarylide yellow and orange pigments, and azo-type red and yellow pigments such as toluidine red, litho red, naphthol red and brown pigments, and combinations thereof.

Lakes generally refer to a colorant prepared from a water-soluble organic dye, (e.g., D&C or FD&C) which has been precipitated onto an insoluble reactive or adsorptive substratum or diluent. The term "D&C" as used herein means drug and cosmetic colorants that are approved for use in drugs and cosmetics by the FDA. The term "FD&C" as used herein means food, drug, and cosmetic colorants which are approved for use in foods, drugs, and cosmetics by the FDA. Certified D&C and FD&C colorants are listed in 21 C.F.R. §74.101 et seq. and include the FD&C colors Blue 1, Blue 2, Green 3, Orange B, Citrus Red 2, Red 3, Red 4, Red 40, Yellow 5, Yellow 6, Blue 1, Blue 2, Orange B, Citrus Red 2, and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Substrates suitable for forming lakes include, without limitation, mica, bismuth oxychloride, sericite, alumina, aluminum, copper, bronze, silver, calcium, zirconium, barium, and strontium, titanated mica, filmed silica, spherical silica, polymethylmethacrylate (PMMA), micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorilionite, microcrystalline cellulose, rice starch, silica, talc, mica, titanium dioxide, zinc laurate, zinc myristate, zinc rosinate, alumina, ahapulgite, calcium carbonate, calcium silicate, dextran, nylon, silica silylate, silk powder, sericite, soy flour, tin oxide, titanium hydroxide, trimagnesium phosphate, walnut shell powder, and mixtures thereof. Suitable lakes include, without limitation, those of red dyes from the monoazo, disazo, Norm, xanthene, or indigoid families, such as Red 4, 6, 7, 17, 21, 22, 27, 28, 30, 31, 33, 34, 36, and Red 40; lakes of yellow pyrazole, monoazo, fluoran, xanthene, quinoline, dyes or salt thereof, such as Yellow 5, 6, 7, 8, 10, and 11; lakes of violet dyes including those from the anthroquinone family, such as Violet 2, as well as lakes of orange dyes, including Orange 4, 5, 10, 11, and the like. Suitable lakes of D&C and FD&C dyes are defined in 21 C.F.R. §82.51.

The coloring agents may be optionally surface treated, for example, to mike the particles more hydrophobic or more dispersible in a vehicle. The surface of the particles may, for example, be covalently or ionically bound to an organic molecule or silicon-based molecule or may be adsorbed thereto, or the particle may be physically coated with a layer of material. The surface treatment compound may be attached to the particle through any suitable coupling agent, linker group, or functional group (e.g., silane, ester, ether, etc). The compound may comprise a hydrophobic portion which may be selected from, for example, alkyl, aryl, ailyl, vinyl, alkyl-aryl, aryl-alkyl, organosilicone, di-organosilicone, dimethicones, methicones, polyurethanes, silicone-polyurethanes, and fluoro- or perfluoro-derivatives thereof. Other hydrophobic modifiers include lauroyl lysine, isopropyl Titanium Triisostearate (ITT), ITT and Dimethicone (ITT/Dimethicone) cross-polymers, ITT and Amino Acid, ITT/Triethoxycaprytylsilarte Crosspolymer, waxes (e.g., carnauba), fatty acids (e.g., stearates), HDI/Trimethylol Hexylactone Crosspolymer, PEG-8 Methyl. Ether Triethoxysilane, aloe, jojoba ester, lecithin, perfluoroalcohol phosphate, and Magnesium Myristate (MM), to name a few.

An optional pigment component includes and alkyl silane surface-treated colorant consisting essentially of or comprising an alumina substrate (e.g., platelet shaped) and a pigment, dye, or lake bonded to the alumina substrate by an alkyl silane surface treatment, Typically, the alkyl slime will be octylsilane, and may be formed by treatment with triethoxy caprylylsilane. Non-limiting examples of such colorants include, but are not limited to, Alumina/Titanium Dioxide/Triethoxycaprylylsilane 1% (COVALUMINE™ Atlas White AS), Alumina/D&C Red Aluminum Lake CTD/Triethoxycaprylylsilane 1% (COVALUMINE™ Red Rose AS), Alumina/D&C Red Aluminum Lake CTD/Triethoxycaprylylsilane 1% (COVALUMINE™ Sonoma Red AS), Alumina/Black Iron Oxide CTD/Triethoxycaprylylsilane 1% (COVALUMINE™ Sonoma Black AS), Alumina/D&C Red #6 Aluminum Lake CTD/Triethoxycaprylylsilane 1% (COVALUMINE™ Fire Red AS), Alumina/Yellow Iron Oxide CTD/Triethoxycaprylylsilane 1% (COVALUMINE™ Sonoma Yellow AS), Alumina/D&C Blue #1 Aluminum Lake CTD/Triethoxycaprylylsilane 1% (COVALUMINE™ Astral Blue AS), Alumina/Carmine CTD/Triethoxycaprylylsilane 1% (COVALUMINE™ Campari AS), Alumina/Yellow #5 CTD/Triethoxycaprylylsilane 1% (COVALUMINE™ Sunburst AS), Alumina/Triethoxycaprylylsilane 1%, and combinations thereof, each of which is available from SENSIENT™ Cosmetic Technologies LCW.

Interference or pearl pigments may also be included. These are typically comprised of micas layered with about 50 to 300 nm films of $TiO_2$, $Fe_2O_3$, or $Cr_2O_3$ or the like. These include white nacreous materials, such as mica covered with titanium oxide or covered with bismuth oxychloride; and colored nacreous materials, such as titanium mica with iron oxides, titanium mica with ferric blue or chromium oxide, titanium mica with an organic pigment of the aforementioned type. If these materials are used, it is preferred that these materials are used collectively in an amount of less than 1.0 wt %. Preferably, the pearlescent component has a bismuth oxychloride based pearlescent ingredient or reflectance pearls. Bismuth oxychloride matches the skin's natural pearlescence more than compounds such as titanium oxide, which provide for a more artificial look. Bismuth oxychloride better mimics the skin's natural reflectance. However, other pearlescent ingredients may be used. A preferred pearlescent component is called CHROMA-LITE, which is a combination of colored pigment bonded to BI-LITE 20 (bismuth oxychloride and mica) using calcium stearate. The CHROMA-LITE component is available in various shades/colors from Englehard Corporation (Iselin, N.J.).

Cosmetically acceptable vehicles: The inventive compositions will typically comprise a cosmetically acceptable vehicle. "Cosmetically acceptable" as used herein means that it is safe for contact with a human integument. The vehicle may comprise a liquid, comprising a single phase, a dual-phase system, or an emulsion. Emulsions include oil-in-water, silicone-in-water, water-in-oil, water-in-silicone, and the like. When formulated as an emulsion, an emulsifier is typically included. Special mention may be made of volatile silicones (e.g., cyclopentasiloxane), hydrocarbons, ester oils, lower alcohols (e.g., ethanol, isopropyl alcohol, etc.), and water.

Emollients: Emollients may be used in the invention, and include, but are not limited to, esters oils, which will typically be the etherification product of an acid of the form $R_4(COOH)_{1-2}$ with an alcohol of the form $R_5(OH)_{1-3}$ where $R_4$ and $R_5$ are each independently linear, branched, or cyclic hydrocarbon groups, optionally containing unsaturated bonds, and having from 1 to 30 carbon atoms, preferably from 2 to 30 carbon atoms, and more preferably, from 3 to 30 carbon atoms, optionally substituted with one or more functionalities including hydroxyl, oxa, oxo, and the like. Preferably, at least one of $R_4$ and $R_5$ comprises at least one fatty chain. The esters defined above will include, without limitation, the esters of mono-acids with mono-alcohols, mono-acids with diols and triols, di-acids with mono-alcohols, and tri-acids with mono-alcohols. Other emollients include dimethicone. Humectants, such as glycerin and other C1-10 polyols or diols may also be included.

Fillers: Fillers can also optionally be added, in an amount from about 1% to about 20%, preferably from about 1% to about 10% by weight of the final composition. Examples of fillers include, but are not limited to, silica, PMMA, nylon, alumina, barium sulfate, or any other filler typically used in such compositions.

Film formers: Polymeric film formers include cellulosics, polyolefins, polyvinyls, polacrylates, polyurethanes, silicones, silicone acrylates, polyamides, polyesters, fluoropolymers, polyethers, polyacetates, polycarbonates, polyimides, rubbers, epoxies, formaldehyde resins, and homopolymers and copolymers of any of the foregoing.

Oils: Suitable non-limiting examples of oils for the oil phase (for example, in an emulsion) include natural and synthetic oils, including animal, vegetable, and petroleum oils; fatty acid triglycerides; fatty acid esters such as octyl palmitate, isopropyl myristate and isopropyl palmitate; ethers such as dicapryl ether; fatty alcohols such as cetyl alcohol, stearyl alcohol and behenyl alcohol; sterols; hydrocarbons such as isooctane, isododecane, isohexadecane, decane, dodecane, tetradecane, tridecane, $C_{8-20}$ isoparaffins, mineral oil, petrolatum, isoeicosane and polyisobutene; $C_{10-30}$ cholesterol/ lanosterol esters; lanolin; and the like. Representative hydrocarbons include paraffinic hydrocarbons available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename PERMETHYL 99A™ are also contemplated to be suitable. Various commercially available $C_{16}$ isoparaffins, such as isohexadecane (having the tradename PERMETHYL®) are also suitable. Silicone oils such as dimethicones, cyclic silicones, and polysiloxanes may also be included in the oil phase. In one embodiment, silicone oils are present in an amount less than about 5% by weight of the oil phase.

Solvents: The cosmetically acceptable vehicle may comprise a volatile solvent. Typically, a volatile solvent may have a vapor pressure of above about 0.01 mmHg at 20° C. Volatile solvents may include volatile $C_{5-12}$ hydrocarbons (e.g., isododecane), aromatic hydrocarbons (e.g., xylenes, toluene, etc.), ketones acetone, methylethyl ketone, etc.), ethers (e.g., diethyl ether, methylethyl ether, etc.), perfluorohydrocarbons, hydrofluoroethers, Freons, esters of acetic acid (e.g., ethylacetate, butylacetate, etc.) and the like. Preferred volatile solvents will be cosmetically acceptable.

Thickeners: Suspending and thickening agents typically include silica gels, gums, clays, fumed silica, fatty acid soaps, and various hydrocarbon gels, and other ingredients that when incorporated into the formulation remain on the surface of keratinous tissues as disclosed in the *International Cosmetic Dictionary and Handbook* (12th Ed.), which is hereby incorporated by reference. Viscosifying agents such as gellants may also be used. Examples include bentone, triglycerides, aluminum stearate, $C_{18}$-$C_{36}$ acid glycol esters, glyceryl tribehenate, glycerol monostearate, alginates, carbomers, celluloses, gums; carageenans, starches or silicates.

Waxes: Waxes which may be used in the invention include, but are not limited to, linear polyethylene, microcrystalline petroleum wax, carnauba wax, lignite wax, ouricouri wax, rice bran wax, castor wax, mortar wax, stearone, acrawax, bayberry wax, castor wax, Japan wax, ozokerite, beeswax, candelilla wax, petrolatum, ceresin wax, cocoa butter, illipe butter, esparto wax, shellac wax, ethylene glycol diesters or triesters of $C_{18}$-$C_{36}$ fatty acids, cetyl palmitate, paraffin wax, hard tallow, lanolin, lanolin alcohol, cetyl alcohol, glyceryl monostearate, sugarcane wax, jojoba wax, stearyl alcohol, silicone waxes, and combinations thereof.

It is understood to those skilled in the art that any other cosmetically acceptable ingredients, i.e., those included in the *CFTA Cosmetic Ingredient Dictionary,* 3rd Ed., may be used.

EXAMPLES

Exemplary cosmetic compositions according to the invention are provided in Tables 1 through 6, below.

TABLE 1

Foundation (Oil-in-Water Emulsion)

| Material | Amount (% wt/wt) |
|---|---|
| Waxes | 3-6 |
| Oils | 8-12 |
| Solvent | 25-60 |
| Colorants | 5-15 |
| EUDRAGIT | 0.2-10 |
| Emollients | 8-12 |
| Other Film Former | 2-5 |
| Thickeners | 1-3 |

TABLE 2

Foundation (Water-in-Oil Emulsion)

| Material | Amount (% wt/wt) |
|---|---|
| Waxes | 0-5% |
| Oils | 25-50% |
| Solvent | 20-35% |
| Colorants | 5-15% |
| EUDRAGIT | 0.2-10% |
| Emollients | 25-50% |
| Other Film Former | 2-5% |
| Thickeners | 0-1% |

TABLE 3

Mascara

| Material | Amount (% wt/wt) |
|---|---|
| Waxes | 15-25% |
| Oils | 0-1% |
| Colorants | 7-10% |
| Solvent | 5-30% |
| EUDRAGIT | 0.2-10% |
| Emollients | 0-1% |
| Other Film Former | 5-25% |
| Thickeners | 1-2% |

TABLE 4

Press Powder

| Material | Amount (% wt/wt) |
|---|---|
| Waxes | 0.5-2% |
| Oils | 2-15% |
| Colorants | 10-30% |
| EUDRAGIT | 0.2-10% |
| Emollients | 2-15% |
| Other Film Former | 0-2% |

TABLE 5

Liquid Eyeshadow

| Material | Amount (% wt/wt) |
|---|---|
| Waxes | 5-15% |
| Oils | 5-20% |
| Colorants | 5-15% |
| Solvent | 10-25% |
| EUDRAGIT | 0.2-10% |
| Emollients | 5-20% |
| Other Film Former | 5-10% |
| Thickeners | 1-3% |

TABLE 6

Aqueous Lip Product

| Material | Amount (% wt/wt) |
|---|---|
| Oils | 0-10% |
| Colorants | 3-15% |
| Solvent | 60-90% |
| EUDRAGIT | 0.2-10% |
| Emollients | 0-10% |
| Other Film Former | 0-5% |
| Thickeners | 0.1-3% |

As used in the Examples, "EUDRAGIT" may be EUDRAGIT® S100 or EUDRAGIT® L100. The inventive cosmetic compositions are expected to have surprising properties, i.e. to remain on the integument for extended periods of time and to be easily removed by modulation of pH conditions or washing.

The invention having been described by the foregoing description of the preferred embodiments, it will be understood that the skilled artisan may make modifications and variations of these embodiments without departing from the spirit or scope of the invention as set forth in the following claims.

We claim:

1. A method for forming a cosmetic film on a human integument comprising: applying to said human integument a cosmetic composition comprising a cosmetically acceptable vehicle, optionally, one or more colorants, and a pH-dependent film-forming polymer of poly(methacrylic acid-co-methyl methacrylate) with a ratio of methacrylic acid to methyl methacrylate of about 1:1 to about 1:2, an acid value of from about 150 to about 350 mg KOH/g, and a weight average molar mass between about 100,000 and about 150,000 g/mol, wherein said polymer is capable of forming an adherent film on a human integument that is resistant to removal by water at a first pH, but readily dispersible or soluble in water at a second pH higher than said first pH, with the proviso that said film forming polymer is not in the form of a microcapsule, wherein said cosmetic composition is a mascara.

2. A method according to claim 1, wherein said second pH is greater than about 5.5.

3. A method according to claim 1, wherein said second pH is greater than about 6.5.

4. A method according to claim 1, wherein said second pH is greater than about 7.5.

5. A method according to claim 1, wherein said ratio of methacrylic acid to methyl methacrylate is about 1:1.

6. A method according to claim 1, wherein said ratio of methacrylic acid to methyl methacrylate is about 1:2.

7. A method according to claim 1, wherein said acid value is from about 150 to about 200 mg KOH/g.

8. A method according to claim 1, wherein said acid value is from about 300 to about 350 mg KOH/g.

9. A method according to claim 1, further comprising contacting said cosmetic composition with soap and water to raise the pH of the human integument from the first pH to the second pH, thereby removing the cosmetic composition from the human integument.

10. A method according to claim 1, wherein said cosmetic composition is a mascara.

11. A cosmetic composition comprising a cosmetically acceptable vehicle, optionally, one or more colorants, and a pH-dependent film-forming polymer of poly(methacrylic acid-co-methyl methacrylate) with a ratio of methacrylic acid to methyl methacrylate of about 1:1 to about 1:2, an acid value of from about 150 to about 350 mg KOH/g, and a weight average molar mass between about 100,000 and about 150,000 g/mol, wherein said polymer is capable of forming an adherent film on a human integument that is resistant to removal by water at a first pH, but readily dispersible or soluble in water at a second pH higher than said first pH, with the proviso that said film forming polymer is not in the form of a microcapsule, wherein said cosmetic composition is a mascara.

12. A composition according to claim 11, wherein said second pH is greater than about 5.5.

13. A composition according to claim 11, wherein said second pH is greater than about 6.5.

14. A composition according to claim 11, wherein said second pH is greater than about 7.5.

15. A composition according to claim 11, wherein said ratio of methacrylic acid to methyl methacrylate is about 1:1.

16. A composition according to claim 11, wherein said ratio of methacrylic acid to methyl methacrylate is about 1:2.

17. A composition according to claim 11, wherein said acid value is from about 150 to about 200 mg KOH/g.

18. A composition according to claim 11, wherein said acid value is from about 300 to about 350 mg KOH/g.

* * * * *